US008168210B2

(12) United States Patent
Ogami

(10) Patent No.: US 8,168,210 B2
(45) Date of Patent: May 1, 2012

(54) PRESSED POWDER COSMETIC COMPOSITION COMPRISING FLAKY GLASS

(75) Inventor: Kazunori Ogami, Kobe (JP)

(73) Assignee: The Procter & Gamble Company, Cincinnati, OH (US)

( * ) Notice: Subject to any disclaimer, the term of this patent is extended or adjusted under 35 U.S.C. 154(b) by 258 days.

(21) Appl. No.: 12/549,006

(22) Filed: Aug. 27, 2009

(65) Prior Publication Data

US 2010/0055140 A1    Mar. 4, 2010

Related U.S. Application Data

(60) Provisional application No. 61/190,437, filed on Aug. 28, 2008.

(51) Int. Cl.
*A61K 8/02* (2006.01)
*A61Q 1/02* (2006.01)

(52) U.S. Cl. ......................... 424/401; 424/63

(58) Field of Classification Search ............ 424/401
See application file for complete search history.

(56) References Cited

U.S. PATENT DOCUMENTS

| | | | |
|---|---|---|---|
| 5,496,544 A | | 3/1996 | Mellul |
| 5,849,333 A | * | 12/1998 | Nordhauser et al. ........ 424/489 |
| 2002/0028220 A1 | | 3/2002 | Kashimoto |
| 2004/0197286 A1 | | 10/2004 | Robert et al. |
| 2005/0049133 A1 | | 3/2005 | Fujiwara |
| 2005/0142084 A1 | * | 6/2005 | Ganguly et al. ............. 424/63 |
| 2005/0232957 A1 | * | 10/2005 | Katz ............................. 424/401 |
| 2007/0048232 A1 | | 3/2007 | Bouchard |
| 2009/0087463 A1 | | 4/2009 | Yagyu |

FOREIGN PATENT DOCUMENTS

| | | |
|---|---|---|
| EP | 1510506 A1 * | 3/2005 |
| FR | 2885298 A | 11/2006 |
| JP | 9-110452 A | 4/1997 |
| JP | 2001-11340 A | 1/2001 |
| JP | 2006-176557 A | 7/2006 |
| JP | 2007-176935 A | 7/2007 |
| JP | 2007-254745 | 10/2007 |
| WO | WO2007/119395 | 10/2007 |

OTHER PUBLICATIONS

Stephanie Postiaux Giada Tonet Ingrid Vervier et al: "Improved long lasting of lipstick using a combination of elastomeric powers and silicone acrylate copolymers", Rearch Disclosure, Mason Publications, Hampshire, GB, vol. 512, No. 10.
PCT International Search Report, date mailed: Jan. 20, 2010, 4 pages.

* cited by examiner

*Primary Examiner* — Richard Schnizer
*Assistant Examiner* — Audrea Buckley
(74) *Attorney, Agent, or Firm* — John G. Powell; Megan C. Hymore

(57) ABSTRACT

The present invention is directed to a pressed powder cosmetic composition, comprising by weight: (a) from about 75% to about 98% of a powder component, the powder component comprising a cosmetic grade flaky glass constituted of components comprising by weight at least 52% silicone dioxide and no more than 5% alkali metal oxide, and wherein the cosmetic grade flaky glass has an average thickness of 0.1-1.0 μm, an average particle diameter of 1-100 μm, and an aspect ratio, obtained by dividing the average particle diameter by the average thickness, of 10 or higher; (b) from about 1% to about 24% of a powder binder, the powder binder comprising sodium stearyl fumarate; and (c) from about 1% to about 25% of a liquid binder.

8 Claims, No Drawings

PRESSED POWDER COSMETIC COMPOSITION COMPRISING FLAKY GLASS

CROSS REFERENCE TO RELATED APPLICATIONS

This application claims the benefit of U.S. Provisional Application No. 61/190,437 filed on Aug. 28, 2008.

FIELD OF THE INVENTION

The present invention relates to pressed powder cosmetic compositions comprising cosmetic grade flaky glass, powder binder and liquid binder.

BACKGROUND OF THE INVENTION

A foundation composition can be applied to the face and other parts of the body to even skin tone and texture and to hide pores, imperfections, fine lines and the like. A foundation composition is also applied to moisturize the skin, to balance the oil level of the skin, and to provide protection against the adverse effects of sunlight, wind, and other environmental factors.

Foundation compositions in the form of solids, such as loose powders and pressed powders are popular among consumers who enjoy the fresh light feeling on the skin. Pressed powder foundations which are packaged in compacts are particularly suitable; as such products can be carried for use.

For pressed powder foundations, long lasting benefit is one of the biggest consumer needs, especially in spring and summer. As is well known in the art, generally skin becomes oilier in spring and summer and drier in winter and autumn. In pressed powder foundations which have low amount of liquid, the wetness of the powder included in the original form is low. For such product form, the powders tend to be wetted by sebum and/or sweat, and thus the color or shade of the foundation may change. Such change of color/shade is a common concern for powder foundations, as such change in shade may be perceived by consumers as make-up wearing off.

Sericite and mica are components of powder foundations functioning as filler and pigment, which provide favorable look, such as translucent or pearlescent, depending on the type of material. When sericite or mica of natural origin is wetted by sebum or sweat, translucency of sericite or mica itself increases, while impurities such as iron oxide contained in the natural sericite or mica become more visible, such that the overall pigment appears as having a dull color. This is believed to be one of the causes of color/shade change.

In order to alleviate the above mentioned problem, several approaches have been taken in formulating powder foundations. One approach is to prohibit sebum or sweat from wetting the powders, for example, by treating powders with coating agents such as fluorine which is known to repel both sweat and sebum. Thus, foundations using fluorine coated pigments provide good wear resistance initially upon application, and over a certain period of time. These foundations containing fluorine coated pigments, however, tend not to be as effective when the foundation is worn for a long time. Another approach is to incorporate a pigment that is already wetted by certain oils, such as taught in JP 2006-176557A (Kanebo), such that the shade change caused by further wetting can be avoided. These foundations are effective in avoiding shade change, however, tend to provide a moist and less light feeling, due to the greater amount of oil incorporated in the entire composition. Accordingly, foundations that have balanced benefits of good resistance to color/shade change, while providing a fresh feel to the skin, are still desired.

JP 9-110452A and WO2007/119395 (Nippon Sheet Glass) disclose flaky glass that is useful for cosmetic use, its physical properties, and manufacturing processes. Cosmetic materials comprising flaky glass is generally disclosed, as having benefits of good spreadability, skin adhesion and transparency, fine texture and feel.

While incorporation of flaky glass in cosmetic compositions provides certain appearance benefits, because of their relatively flat and thin shape, they may cause difficulty in cake press formability. Cake press formability affects product performance such as pay off, and also affects shock resistance of the pressed cake. Suitable binders compatible with flaky glass which can form powder foundations using common pressing procedures are desired. Further, there is room for improving the adhesion of flaky glass on the skin.

FR 2885298A (LCW) discloses the use of sodium stearyl fumarate as a binding agent for cosmetic compositions which are pressed to be in a tablet form.

Based on the foregoing, there is a need for a pressed powder cosmetic composition which has balanced benefits in terms of shine control, transfer resistance, color stability, good spreadability when applying on the skin, good adhesion on the skin, fine texture, fresh light feel on the skin, cake press formability, shock resistance and good pay off.

None of the existing art provides all of the advantages and benefits of the present invention.

SUMMARY

The present invention is directed to a pressed powder cosmetic composition, comprising by weight:
(a) from about 75% to about 98% of a powder component, the powder component comprising a cosmetic grade flaky glass constituted of components comprising by weight at least 52% silicone dioxide and no more than 5% alkali metal oxide, and wherein the cosmetic grade flaky glass has an average thickness of 0.1-1.0 μm, an average particle diameter of 1-100 μm, and an aspect ratio, obtained by dividing the average particle diameter by the average thickness, of 10 or higher;
(b) from about 1% to about 24% of a powder binder, the powder binder comprising sodium stearyl fumarate; and
(c) from about 1% to about 25% of a liquid binder.

The pressed powder cosmetic compositions of the present invention provide balanced benefits of shine control, transfer resistance, color stability, good spreadability when applying on the skin, good adhesion on the skin, and fresh light feel on the skin, good cake press formability, shock resistance and good pay off. The pressed powder cosmetic composition of the present invention is particularly useful for use in cosmetic products having the function of foundations, eyebrows, eyeshadows, blushers, highlighters, concealers, and others.

These and other features, aspects, and advantages of the present invention will become evident to those skilled in the art from a reading of the present disclosure with the appended claims.

DETAILED DESCRIPTION

While the specification concludes with claims particularly pointing out and distinctly claiming the invention, it is believed that the present invention will be better understood from the following description.

All cited references are incorporated herein by reference in their entireties. Citation of any reference is not an admission regarding any determination as to its availability as prior art to the claimed invention.

Herein, "comprising" means that other elements which do not affect the end result can be added. This term encompasses the terms "consisting of" and "consisting essentially of".

All percentages, parts and ratios are based upon the total weight of the compositions of the present invention, unless otherwise specified. All such weights as they pertain to listed ingredients are based on the active level and, therefore do not include carriers or by-products that may be included in commercially available materials.

All ingredients such as actives and other ingredients useful herein may be categorized or described by their cosmetic and/or therapeutic benefit or their postulated mode of action. However, it is to be understood that the active and other ingredients useful herein can, in some instances, provide more than one cosmetic and/or therapeutic benefit or operate via more than one mode of action. Therefore, classifications herein are made for the sake of convenience and are not intended to limit an ingredient to the particularly stated application or applications listed.

Pressed Powder Cosmetic Composition

The pressed powder cosmetic composition of the present invention comprises components of powder, powder binder and liquid binder.

Cosmetic compositions of the present invention and their respective components are listed herein below, comprising:
 (a) from about 75% to about 98% of a powder component, the powder component comprising a cosmetic grade flaky glass constituted of components comprising by weight at least 52% silicone dioxide and no more than 5% alkali metal oxide, and wherein the cosmetic grade flaky glass has an average thickness of 0.1-1.0 μm, an average particle diameter of 1-100 μm, and an aspect ratio, obtained by dividing the average particle diameter by the average thickness, of 10 or higher;
 (b) from about 1% to about 24% of a powder binder, the powder binder comprising sodium stearyl fumarate; and
 (c) from about 1% to about 25% of a liquid binder.

The pressed powder cosmetic composition of the present invention can be prepared by a common process known to the artisan, that is uniformly mixing the powder binder, and any other solid material; mixing the product of previous step with the liquid binder and any other liquid material, and pressing the finally resulting mixture under pressure of from about 3.0 to about 7.0 Mpa.

Powder Component

The composition of the present invention comprises a powder component comprising at least a flaky glass. The amount of powder component included in the present composition is sufficient for providing a pressed powder cosmetic composition, ranging from about 75% to about 98%. Compositions of the present invention will also comprise other powders, which are discussed in detail below.

Flaky Glass

Flaky glass useful in the present invention is of cosmetic grade, which can be safely used in cosmetic compositions, constituted of components comprising by weight of at least 52% silicone dioxide and no more than 5% alkali metal oxide, and wherein the cosmetic grade flaky glass has an average thickness of 0.1-1.0 μm, an average particle diameter of 1-100 μm, and an aspect ratio of 10 or higher. Generally, such cosmetic grade flaky glass are those that are transparent and smooth, and has less impurity, thus can be used to replace other transparent or translucent pigments and fillers commonly used in formulating solid foundation compositions, such as sericite, mica and talc. It has been unexpectedly found that the combination of flaky glass and powder binders can deliver a solid cosmetic composition with the benefit of long lasting effect, light feel, good spreadability, and good adhesion to the skin. Further, when the combination is incorporated in pressed powder forms, it has been found that favorable cake press formability, shock resistance and good pay off are achieved.

Particularly useful flaky glass herein includes those described in WO 2007/119395.

The physical properties of the flaky glass of the present invention are measured using the following methods. The thickness is measured by the interference fringe method using an Interpha-ko made by Carl Zeiss. The particle size is measured by laser diffraction using an SALD-2000 made by Shimadzu Corporation. The ratio of particle size to thickness (average particle diameter/average thickness) is obtained and regarded as the aspect ratio.

The flaky glass of the present invention may be unmodified, surface coated, or complexed with other pigments.

In one embodiment of the present invention, the flaky glass is hydrophobically surface treated. Preferably the flaky glass is surface treated with silicone. Commercially available flaky glass highly useful herein includes flaky glass with silicone surface treatment with the tradename SILKY FLAKE available from Nippon Sheet Glass.

In another embodiment of the present invention, the flaky glass is a complex pigment coated with titania and rare metal, such as those in JP2001-11340A, which provide pearlescence and brightness. In yet another embodiment, the flaky glass encompasses dispersed colored particles such as ultramarine, such as those in JP 2007-176935A which provides a colored pigment that does not show dull color over time.

The composition of the present invention preferably comprises by weight from about 10% to about 50% of the flaky glass, more preferably, from about 15% to about 40% of the flaky glass. When used at such preferred levels, it is believed that compositions are provided a particularly favorable transparent look and color stability. Such benefits are particularly useful for power foundations.

Other Powders

Besides the flaky glass described above, the composition of the present invention may comprise other powders for making the pressed powder cosmetic composition. Other powders are preferably included for providing desired characteristics of the product, such as skin feel benefits.

One preferred other powder for use herein is synthetic mica. Synthetic mica may provide similar color stability benefits as the flaky glass described above, while also being relatively inexpensive than the flaky glass. Synthetic mica may be used to replace part of the flaky glass in formulating compositions of the present invention. When used, the amount of synthetic mica contained in the present composition is preferably from about 1% to abut 88% by weight, more preferably from about 3% to about 30% by weight. Commercially available synthetic mica include, for example, synthetic fluorphologopite coated with dimethicone with trade name SA-SYNTHETIC MICA PDM-8W from MIYOSHI KASEI, INC.

The other powders useful herein include clay mineral powders that can be base powders and coloring powders, such as talc, silica, magnesium silicate, calcium silicate, aluminum silicate, titanium dioxide and iron oxide, bentonite and montomorilonite, with or without surface treatment, for example silicone treatment. Other inorganic powders useful herein include pearl pigments such as alumina, barium sulfate, calcium secondary phosphate, calcium carbonate, zirconium oxide, zinc oxide, hydroxy apatite, iron titate, ultramarine blue, Prussian blue, chromium oxide, chromium hydroxide, cobalt oxide, cobalt titanate, titanium oxide coated mica, boron nitride, and other complex powders. Organic powders useful herein include polyester, polyethylene, polystyrene, methyl metharylate resin, cellulose, 12-nylon, 6-nylon, styrene-acrylic acid copolymers, poly proprylene, vinyl chloride polymer, tetrafluoroethylene polymer, starch, silk, fish scale guanine, laked tar color dyes, and laked natural color dyes. Such inorganic and organic powders may be treated with a hydrophobical treatment agent, including: silicone such as Methicone, Dimethicone fatty material such as stearic acid; metal soap such as aluminium dimyristate; aluminium hydrogenated tallow glutamate, hydrogenated lecithin, lauroyl lysine, aluminium salt of perfluoroalkyl phosphate, and mixtures thereof.

Commercially available other powders include, for example, HDI/Trimethylol Hexyllactone Crosspolymer of the trade name DAIMICBEAZ UCN-8150CM CLEAR available from DAINICHI SEIKA COLOR & CHEMICAL MFG CO., LTD, calcium aluminum borosilicate coated with titanium dioxide and tin oxide under the trade name of MICROGLAS METASHINE MC1040RS available from NIPPON SHEET GLASS CO., LTD.

In one preferred embodiment, the composition of the present invention is substantially free of natural mica and sericite. Compositions substantially free of natural mica and sericite are expected to provide improved color stability. Color stability of the pressed powder composition in terms of shade change before and after wetted by oil can be tested according to the method titled "Shade change" described in the Examples.

In one preferred embodiment, the composition of the present invention is substantially free of fluorine-coated pigments. While fluorine coating may be useful for providing good resistance against water and sebum, it will be of exceptional benefit from environmental consideration not to use fluorine-coated ingredients.

Powder Binder

The composition of the present invention comprises a powder binder comprising at least sodium stearyl fumarate, for example that under the trade name of COVAFLUID FS available from DAITO KASEI KOGYO CO., LTD. The powder binder may further comprise a component selected from the group consisting of zinc stearate, magnesium stearate, calcium stearate, and mixtures thereof. It has been unexpectedly found that the powder binder of the present invention, when combined with flaky glass described above, can deliver a pressed powder cosmetic composition with good shade change control, adhesion to the skin, and holding efficacy of other components such as the other powders, good cake press formability and shock resistance.

Without being bound by theory, because of their relatively flat and thin shape, flaky glass may cause difficulty in cake press formability. Namely, when pressed at commonly used conditions, it may provide a cake of inferior shock resistance. On the other hand, if pressed at a very high pressure, a cake of acceptable shock resistance may be made; however, the cake would be so hard that the pay off upon application to the skin would become too small. Such difficulty in cake press formability is particularly noticeable when at least about 10% of flaky glass is used in the entire composition. It has been unexpectedly found that the powder binder of the present invention can provide good cake press formability to compositions including flaky glass, even when using common pressing conditions well known in the art. Further, the combination of the flaky glass and powder binder provides benefits such as long lasting effect, color stability, light feel, and good adhesion to the skin, while also providing good spreadability when applying on the skin, despite the good adhesion. When incorporated in pressed powder forms, the pressed powder cosmetic composition of the present invention preferably comprises by weight from about 1% to about 24% of the powder binder, more preferably, from about 2% to about 10% of the powder binder. When used at such preferred levels, it is believed that compositions provide particularly favorable cake press formability and shock resistance. Such benefits are particularly useful for power foundations, and can be evaluated according to the method titled "Shock Resistance" described in the Examples.

Liquid Binder

The present composition may further comprise other binder material for providing certain product forms, and additional usage benefits. Useful herein are liquid binders which keep powders, in general, from scattering upon use and carriage. The amount and type of liquid binder is selected depending on the desired characteristic of the product, for example, product form coverage, adhesion to the skin, and various skin feel. The liquid binder herein may also be used for providing certain benefits such as UV protection, or for dissolving skin active agents which otherwise could not be incorporated in the composition.

Silicone oils are useful as the binder component herein. Particularly useful are those which have low viscosity but are not too volatile, preferably those having a viscosity of less than about 400 mPas and a volatility as such that not more than 35% of the silicone oil evaporates after standing at 150° C. at normal pressure for 24 hours. Such silicone oils are believed to enhance the fresh and light feel when the composition is applied to the skin.

Silicone oils useful herein also include polyalkyl or polyaryl siloxanes with the following structure (I)

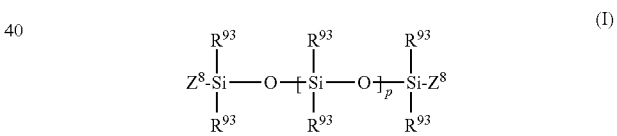

(I)

wherein $R^{93}$ is alkyl or aryl, and p is an integer from about 7 to about 100. $Z^8$ represents groups which block the ends of the silicone chains. The alkyl or aryl groups substituted on the siloxane chain ($R^{93}$) or at the ends of the siloxane chains $Z^8$ can have any structure as long as the resulting silicone remains fluid at room temperature, is dispersible, is neither irritating, toxic nor otherwise harmful when applied to the skin, is compatible with the other components of the composition, and is chemically stable under normal use and storage conditions. Suitable $Z^8$ groups include hydroxy, methyl, methoxy, ethoxy, propoxy, and aryloxy. The two $R^{93}$ groups on the silicon atom may represent the same group or different groups. Preferably, the two $R^{93}$ groups represent the same group. Suitable $R^{93}$ groups include methyl, ethyl, propyl, phenyl, methylphenyl and phenylmethyl. The preferred silicone compounds are polydimethylsiloxane, polydiethylsiloxane, and polymethylphenylsiloxane. Polydimethylsiloxane, which is also known as dimethicone, is especially preferred. The polyalkylsiloxanes that can be used include, for example, polydimethylsiloxanes. Polyalkylaryl siloxane fluids can also be used and include, for example, polymethylphenylsiloxanes.

Commercially available silicone oils useful herein include methylphenyl polysiloxane with tradenames KF56 available from ShinEtsu Chemical Co., Ltd., SF 1075 METHYL PHENYL FLUID available from the General Electric Company, 556 COSMETIC GRADE FLUID available from Dow Corning, and polydimethylsiloxane having less than 50 mPas with tradenames SH200 available from Dow Corning and the VISCASIL and SF96 series available from the General Electric Company.

Liquid binders useful herein can be various grades of mineral oils. Mineral oils are liquid mixtures of hydrocarbons that are obtained from petroleum. Specific examples of suitable hydrocarbons include paraffin oil, mineral oil, dodecane, isododecane, hexadecane, isohexadecane, eicosane, isoeicosane, tridecane, tetradecane, polybutene, polyisobutene, and mixtures thereof.

Still other oils useful as additional binder material herein are, for example, tridecyl isononanoate, isostearyl isostearate, isocetyl isosteatrate, isopropyl isostearate, isodecyl isonoanoate, cetyl octanoate, isononyl isononanoate, diisopropyl myristate, diisostearyl malate, isocetyl myristate, isotridecyl myristate, isopropyl myristate, isostearyl palmitate, isocetyl palmitate, isodecyl palmitate, isopropyl palmitate, octyl palmitate, caprylic/capric acid triglyceride, glyceryl tri-2-ethylhexanoate, neopentyl glycol di(2-ethyl hexanoate), diisopropyl dimerate, tocopherol, tocopherol acetate, avocado oil, camellia oil, turtle oil, macadamia nut oil, corn oil, mink oil, olive oil, rapeseed oil, eggyolk oil, sesame oil, persic oil, wheat germ oil, pasanqua oil, castor oil, linseed oil, safflower oil, cotton seed oil, perillic oil, soybean oil, peanut oil, tea seed oil, kaya oil, rice bran oil, china paulownia oil, Japanese paulownia oil, jojoba oil, rice germ oil, glycerol trioctanate, glycerol triisopalmiatate, trimethylolpropane triisostearate, isopropyl myristate, glycerol tri-2-ethylhexanoate, pentaerythritol tetra-2-ethylhexanoate, lanolin, liquid lanolin, liquid paraffin, squalane, vaseline, cholesteryl derivatives such as cholesteryl 12-hydroxystearate, cholesteryl macadamiate, cholesteryl stearate, succinic acid copolymer such as PPG-7 polypropyleneglycol oligosuccinate(35 P.O.), and mixtures thereof. Commercially available oils include, for example, tridecyl isononanoate with tradename CRODAMOL TN available from Croda, HEXALAN available from Nisshin Seiyu, tocopherol acetates available from Eisai, cholesteryl 12-hydroxystearate with tradename SALACOS HS available from Nisshin Oil Mills, Ltd., and cholesteryl macadamiate with tradename YOFCO MAC available from Nippon Fine Chemical Co., Ltd.

A wide variety of oils having UV protecting benefit are suitable for use herein, including those which are typically called UV protecting agents. Preferred among those UV protecting agents are those selected from 2-ethylhexyl-p-methoxycinnamate (commercially available as PARSOL MCX), butylmethoxydibenzoyl-methane, 2-hydroxy-4-methoxybenzo-phenone, 2-phenylbenzimidazole-5-sulfonic acid, octyldimethyl-p-aminobenzoic acid, octocrylene, 2-ethylhexyl N,N-dimethyl-p-aminobenzoate, p-aminobenzoic acid, 2-phenylbenzimidazole-5-sulfonic acid, octocrylene, oxybenzone, homomenthyl salicylate, octyl salicylate, 4,4'-methoxy-t-butyldibenzoylmethane, 4-isopropyl dibenzoylmethane, 3-benzylidene camphor, 3-(4-methylbenzylidene) camphor, and those by tradenames EUSOLEX 6300, OCTOCRYLENE, PARSOL 1789. These oils can be selected for providing a desired Sun Protection Factor (SPF). SPF is a commonly used measure of photoprotection of a sunscreen against erythema. See Federal Register, Vol. 43, No. 166, pp. 38206-38269, Aug. 25, 1978.

Useful liquid binders here also include emulsifiers including silicone emulsifiers and non-silicone emulsifiers. The emulsifier is selected depending on the other components of the composition of the present invention, and provides the desired emulsification or dispersion characteristics. Suitable emulsifiers have an HLB value of from about 4 to about 14. Emulsifiers having an HLB value outside of these ranges can be used in combination with other emulsifiers to achieve an effective weighted average HLB for the combination that falls within these ranges.

Useful silicone emulsifiers include dimethicone copolyols. These materials are polydimethyl siloxanes which have been modified to include polyether side chains such as polyethylene oxide chains, polypropylene oxide chains, mixtures of these chains, and polyether chains containing moieties derived from both ethylene oxide and propylene oxide. Other examples include alkyl-modified dimethicone copolyols, i.e., compounds which contain C2-C30 pendant side chains. Still other useful dimethicone copolyols include materials having various cationic, anionic, amphoteric, and zwitterionic pendant moieties. Examples of commercially available dimethicone copolyols useful herein sold by Dow Corning Corporation are Dow Corning® 190, 193, Q2-5220, 2501 Wax, 2-5324 fluid, and 3225C (this later material being sold as a mixture with cyclomethicone). Cetyl dimethicone copolyol is commercially available as a mixture with polyglyceryl-4 isostearate (and) hexyl laurate and is sold under the tradename ABIL® WE-09 (available from Goldschmidt). Cetyl dimethicone copolyol is also commercially available as a mixture with hexyl laurate (and) polyglyceryl-3 oleate (and) cetyl dimethicone and is sold under the tradename ABIL® WS-08 (also available from Goldschmidt). Other nonlimiting examples of dimethicone copolyols also include lauryl dimethicone copolyol, dimethicone copolyol acetate, diemethicone copolyol adipate, dimethicone copolyolamine, dimethicone copolyol behenate, dimethicone copolyol butyl ether, dimethicone copolyol hydroxy stearate, dimethicone copolyol isostearate, dimethicone copolyol laurate, dimethicone copolyol methyl ether, dimethicone copolyol phosphate, and dimethicone copolyol stearate. See International Cosmetic Ingredient Dictionary, Fifth Edition, 1993.

The pressed powder form compositions of the present invention are preferably substantially free of either wax or gelling agent for providing better fresh light feel on the skin.

Additional Components

The compositions hereof may further contain additional components which are commonly used in cosmetic products, e.g., for providing aesthetic or functional benefit to the composition or personal surface, such as sensory benefits relating to appearance, smell, or feel, therapeutic benefits, or prophylactic benefits (it is to be understood that the above-described required materials may themselves provide such benefits). When included, the amount is kept to no more than about 10% by weight of the composition.

Examples of suitable topical ingredient classes include: powders and pigments that are not listed above, anti-chelating agents, abrasives, astringents, dyes, essential oils, fragrance, film forming polymers, solubilizing agents, anti-caking agents, antifoaming agents, binders, buffering agents, bulking agents, denaturants, pH adjusters, propellants, reducing agents, sequestrants, cosmetic biocides, and preservatives.

EXAMPLES

The following examples further describe and demonstrate the preferred embodiments within the scope of the present invention. The examples are given solely for the purpose of illustration, and are not to be construed as limitations of the present invention since many variations thereof are possible without departing from its spirit and scope. Where applicable, ingredients are identified by chemical or CTFA name, or otherwise defined below.

The following are pressed power cosmetic compositions for use on skin, method of preparation thereof, and technical assessment of their characteristics thereof. Examples 1-12 are pressed powder cosmetic compositions according to the present invention, while Comparative Examples 1-4 are those that are not according to the present invention.

These embodiments represented by the previous examples are useful as pressed powder cosmetic products. Examples 1-4 and 7 are useful as pressed powder foundations, Example

TABLE 1

Composition of Examples 1-7

| No | Component | Ex. 1 | Ex. 2 | Ex. 3 | Ex. 4 | Ex. 5 | Ex. 6 | Ex. 7 |
|---|---|---|---|---|---|---|---|---|
| 1 | Flaky Glass with Dimethicone *1 | 10 | 25 | 25 | 40 | 15 | 23 | 15 |
| 2 | Synthetic Fluorphologopite coated with Dimethicone *2 | 10 | 5 | | | | | |
| 3 | Talc coated with Methicone | 35.95 | 24.45 | 20.45 | 18.45 | 39.35 | 18.7 | 54.2 |
| 4 | Calcium Aluminum Borosilicate coated with Titanium Dioxide and Tin Oxide *4 | | | | | 15 | 5 | |
| 5 | Titanium Dioxide coated with Methicone | 12 | 10.5 | 10.5 | 12 | 0.25 | 27 | 4 |
| 6 | Polymethyl Methacrylate Crosspolymer | 10 | 5 | 10 | 10 | 9 | 8 | 5 |
| 7 | Nylon-6 | | | 10 | | | | |
| 8 | Nylon-12 | | | | 10 | | | |
| 9 | Silica | 5 | 3 | | | 3 | | 3 |
| 10 | HDI/Trimethylol Hexyllactone Crosspolymer *3 | | | | 2 | | | |
| 11 | Iron Oxide coated with Methicone | 2.5 | 2.5 | 2.5 | 2.5 | 1.1 | 5.8 | 0.5 |
| 12 | Sodium Stearyl Fumarate *5 | 2 | 4 | 4 | 8 | 9 | 4 | 7 |
| 13 | Zinc Stearate | | | 4 | | | | 3 |
| 14 | Dimethicone | 8 | 6 | 5 | 4.5 | | 4 | 3 |
| 15 | Ethylhexyl Methoxycinnamate | 4 | 4 | 4 | 4 | 4.7 | 4 | 4.7 |
| 16 | PPG-7/Succinic Acid Copolymer | | | | 2 | | | |
| 17 | Squalane | | | | | 3 | | |
| 18 | Phenoxyethanol | | | | | 0.3 | | 0.3 |
| 19 | Methylparaben | 0.35 | 0.35 | 0.35 | 0.35 | 0.1 | 0.3 | 0.1 |
| 20 | Propylparaben | 0.1 | 0.1 | 0.1 | 0.1 | 0.2 | 0.1 | 0.2 |
| 21 | Sodium Dehydroacetate | 0.1 | 0.1 | 0.1 | 0.1 | | 0.1 | |
| | total | 100 | 100 | 100 | 100 | 100 | 100 | 100 |

Definitions of Components
*1 Flaky Glass with Dimethicone: SILKY FLAKE available from NIPPON SHEET GLASS CO., LTD.
*2 Synthetic Fluorphologopite coated with Dimethicone: SA-SYNTHETIC MICA PDM-8W available from MIYOSHI KASEI, INC.
*3 HDI/Trimethylol Hexyllactone Crosspolymer: DAIMICBEAZ UCN-8150CM CLEAR available from DAINICHI SEIKA COLOR & CHEMICAL MFG CO., LTD.
*4 Calcium Aluminum Borosilicate coated with Titanium Dioxide and Tin Oxide: MICROGLAS METASHINE MC1040RS available from NIPPON SHEET GLASS CO., LTD.
*5 Sodium Stearyl Fumarate: COVAFLUID FS available from DAITO KASEI KOGYO CO., LTD.

Method of Preparation

The cosmetic compositions of Examples 1-7 are prepared as follows: Components 1-13 and 19-21 are mixed by a mixer to make a pigment mixture. After that, components 14-18 are added to the pigment mixture and mixed by a mixer. The obtained composition is pulverized and pressed in a tray with 3.0 -7.0 MPa pressure and set into a compact, for example for powder foundation. The pressure can be in the range of 4.0-6.0 MPa; for blusher the pressure can be in the range of 6.0-7.0 MPa; for concealer, the pressure can be in the range of 3.0-5.0 MPa.

5 is useful as a pressed powder blusher, and Example 6 is useful as a pressed powder concealer.

When applied on the facial skin, they provide many advantages. For example, they can provide balanced benefits in terms of shine control, transfer resistance, color stability, good spreadability when applying on the skin, good adhesion on the skin, fine texture, fresh light feel on the skin, cake press formability, shock resistance and good pay off.

Examples 8-12 and Comparative Examples 1-4 are pressed powder foundations.

TABLE 2

Composition of Examples 8-12

| No | Component | Ex. 8 | Ex. 9 | Ex. 10 | Ex. 11 | Ex. 12 |
|---|---|---|---|---|---|---|
| 1 | Flaky Glass with Dimethicone *1 | 25 | 20 | 25 | 25 | 25 |
| 2 | Talc coated with Methicone | 37.562 | 37.562 | 33.562 | 40.562 | 39.562 |
| 3 | Synthetic Fluorphologopite coated with Dimethicone *2 | | 5 | | | |
| 4 | Mica coated with Dimethicone | | | | | |
| 5 | Iron Oxide coated with Methicone | 2.388 | 2.388 | 2.388 | 2.388 | 2.388 |
| 6 | Titanium Dioxide coated with Methicone | 12 | 12 | 12 | 12 | 12 |

TABLE 2-continued

Composition of Examples 8-12

| No | Component | Ex. 8 | Ex. 9 | Ex. 10 | Ex. 11 | Ex. 12 |
|---|---|---|---|---|---|---|
| 7 | Polymethyl Methacrylate Crosspolymer | 10 | 10 | 10 | 10 | 10 |
| 8 | Sodium Stearyl Fumarate *5 | 4 | 4 | 4 | 1 | 2 |
| 9 | Zinc Stearate | | | 4 | | |
| 10 | Dimethicone | 4.5 | 4.5 | 4.5 | 4.5 | 4.5 |
| 11 | Ethylhexyl Methoxycinnamate | 4 | 4 | 4 | 4 | 4 |
| 12 | Methylparaben | 0.35 | 0.35 | 0.35 | 0.35 | 0.35 |
| 13 | Propylparaben | 0.1 | 0.1 | 0.1 | 0.1 | 0.1 |
| 14 | Sodium Dehydroacetate | 0.1 | 0.1 | 0.1 | 0.1 | 0.1 |
| | Total | 100 | 100 | 100 | 100 | 100 |

TABLE 3

Composition of Comparative Examples 1-4

| No | Component | Com Ex. 1 | Com Ex. 2 | Com Ex. 3 | Com Ex. 4 |
|---|---|---|---|---|---|
| 1 | Flaky Glass with Dimethicone *1 | 25 | 25 | | 25 |
| 2 | Talc coated with Methicone | 41.562 | 37.562 | 37.562 | 37.562 |
| 3 | Synthetic Fluorphologopite coated with Dimethicone *2 | | | | |
| 4 | Mica coated with Dimethicone | | | 25 | |
| 5 | Iron Oxide coated with Methicone | 2.388 | 2.388 | 2.388 | 2.388 |
| 6 | Titanium Dioxide coated with Methicone | 12 | 12 | 12 | 12 |
| 7 | Polymethyl Methacrylate Crosspolymer | 10 | 10 | 10 | 10 |
| 8 | Sodium Stearyl Fumarate *5 | | | 4 | |
| 9 | Zinc Stearate | | | | |
| 10 | Dimethicone | 4.5 | 8.5 | 4.5 | 1 |
| 11 | Ethylhexyl Methoxycinnamate | 4 | 4 | 4 | 4 |
| 12 | Methylparaben | 0.35 | 0.35 | 0.35 | 0.35 |
| 13 | Propylparaben | 0.1 | 0.1 | 0.1 | 0.1 |
| 14 | Sodium Dehydroacetate | 0.1 | 0.1 | 0.1 | 0.1 |
| 15 | Diisostearyl malate | | | | 7.5 |
| | Total | 100 | 100 | 100 | 100 |

The cosmetic compositions of above Table 2 and Table 3 are prepared as follows: Components 1-9 and 12-14 are mixed by a mixer to make a pigment mixture. After that, components 10-11 and 15 are added to the pigment mixture and mixed by a mixer. The obtained composition is pulverized and pressed in a tray with 5.0 MPa pressing pressure.

Method of Technical Test

1. Shock Resistance

The pressed powder composition of the present invention can be pressed under normal pressure, for providing a product which maintains good shock resistance while keep good pay off. Such shock resistance is suitably quantitatively measured by the Drop Test herein defined:

1) Pressed powder product is dropped from a height of 30.5 cm using drop test apparatus, which is commonly used in the Industry for said test purpose;

2) The pressed powder product is observed by the naked eye to check if pressed powder product has any visible damage.

Pressed powder products of the Examples 8-10 and 12 and Comparative Example 1 were dropped from a 30.5 cm height for a certain number of times to evaluate shock resistance of the 5 products. Those compositions were evaluated by the number of times these pressed powder products endured the drop test with no visible damage observed by naked eyes. For each test product, the test is conducted 3 times, and the average of the 3 test results is recorded. Those endured with an average number of 5 or more drops are rated as ○ (pass); while those endured<5 drops are rated as×(not pass).

Drop test results are shown in the following table 4.

TABLE 4

| | Drop test | | | | |
|---|---|---|---|---|---|
| | Ex. 8 | Ex. 9 | Ex. 10 | Ex. 12 | Com Ex. 1 |
| Average times Endured | 11.3 (○) | 11.0 (○) | 10.0 (○) | 8.3 (○) | 3.6 (X) |

2. Shade Change

The present composition has good color stability even when wetted with sweat and sebum. Color stability is suitable quantitatively measured by lack of shade change, which can be measured by color computer (SpectraFlash 600 Plus; Datacolor International Company) as delta E value of the colorimetric data before and after silicone oil was applied to the composition and wetted until max point of oil absorption. Hunter L-a-b color system is used for such colorimetric measurement.

Shade change test result is shown in the following table 5.

TABLE 5

| Shade change | | | | |
|---|---|---|---|---|
| | Ex. 8 | Ex. 9 | Ex. 10 | Com Ex. 3 |
| Shade change (∠E) | 6.14 | 6.10 | 6.05 | 7.04 |

3. Sensory

The pressed powder cosmetic compositions of the present invention provide sensory benefits such as good spreadability when applying on the skin, good adhesion on the skin, and fresh light feel on the skin, and good pay off. An expert panel of 8 panelists was prepared for a sensory test. Panelists applied foundations of above mentioned Example 8 and Comparative Example 4 on their fingers and forearms, and evaluated about directed questions (DQs) as listed in Table 6. The evaluations a-d and e-g respectively correspond to sensory rating based on finger application and forearm application, while overall rating corresponds to a general evaluation of both finger and forearm. The number and percentage of panelists who answered "I think Example 8 is better" is described.

TABLE 6

| Sensory test | |
|---|---|
| Overall Rating | 88% (7) |
| a. Foundation particles are fine | 88% (7) |
| b. Foundation particles are silky/smooth ("nameraka" in Japanese) | 75% (6) |
| c. Foundation particles are dry/smooth ("sarasara" in Japanese) | 88% (7) |
| d. Foundation particles are light | 88% (7) |
| e. Good sensory during application | 88% (7) |
| f. Leaves skin smooth ("sarasara" in Japanese) | 75% (6) |
| g. Light feeling | 75% (6) |

Evaluation

Comparative Example 1, devoid of the powder binder component and devoid of sodium stearyl fumarate, was evaluated as "x (not pass)" in shock resistance by Drop test, with the average endured times being 3.6, as opposing to the result of Example 8-10 and 12 having the average endured times over 8.

Comparative Example 3, having 25% mica coated with Dimethicone as powder component while not using flaky glass, was evaluated as having higher calorimetric change (∠E) of 7.04 compared to the result of Example 8-10 having ∠E value of around 6.

Comparative Example 4, having no sodium stearyl fumarate but instead a certain amount of liquid binders (1% silicone oil and 7.5% Ester Oil), was evaluated together with the cosmetic composition of the invention in the sensory test. The comparison test result shows that the cosmetic composition of the invention provides better sensory results.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A pressed powder cosmetic composition, comprising by weight:
   a) from about 75% to about 98% of a powder component, the powder component comprising a cosmetic grade flaky glass constituted of components comprising by weight at least 52% silicon dioxide and no more than 5% alkali metal oxide, and wherein the cosmetic grade flaky glass has an average thickness of 0.1-1.0 μm, an average particle diameter of 1-100 μm, and an aspect ratio, obtained by dividing the average particle diameter by the average thickness, of 10 or higher;
   b) from about 1% to about 24% of a powder binder to help hold the composition in a pressed powder configuration, the powder binder comprising sodium stearyl fumarate; and
   c) from about 1% to about 25% of a liquid binder.

2. The cosmetic composition of claim 1, comprising by weight from about 10% to about 50% of the cosmetic grade flaky glass.

3. The cosmetic composition of claim 1, comprising by weight from about 2% to about 10% of the powder binder.

4. The cosmetic composition of claim 1, wherein the composition is free of wax and gelling agent.

5. The cosmetic composition of claim 1 wherein the powder component further comprises synthetic mica.

6. The cosmetic composition of claim 1, wherein the composition is free of natural mica.

7. The cosmetic composition of claim 1, wherein the composition is free of fluorine-coated pigment.

8. The cosmetic composition of claim 1, wherein said composition is a cosmetic product selected from the group consisting of foundation, eyeshadow, blusher, highlighter, and concealer.

* * * * *